United States Patent [19]

Takahashi et al.

[11] Patent Number: 4,829,069
[45] Date of Patent: May 9, 1989

[54] 4-THIOQUINAZOLINE DERIVATIVES AS ANTIULCER AGENTS

[75] Inventors: Toshihiro Takahashi, Kawagoe; Koichi Nakamaru, Ohimachi; Yoshikuni Suzuki, Ohmiya; Tatsuo Horaguchi, Fujimi, all of Japan

[73] Assignee: Nisshin Flour Milling Co., Ltd., Japan

[21] Appl. No.: 175,518

[22] Filed: Mar. 31, 1988

[30] Foreign Application Priority Data

Mar. 31, 1987 [JP] Japan .................................. 62-76244
Oct. 2, 1987 [JP] Japan ................................ 62-250388

[51] Int. Cl.⁴ .................. C07D 401/00; C07D 239/72; A61K 31/505.
[52] U.S. Cl. ..................... 514/259; 544/284; 544/287
[58] Field of Search ................. 544/284, 287; 514/259

[56] References Cited

U.S. PATENT DOCUMENTS 4,349,674   9/1982   Freed et al. ........................... 514/259
4,665,075   5/1987   Vandenberk et al. ............... 544/284

FOREIGN PATENT DOCUMENTS 209062   9/1987   Japan .................................... 514/259

Primary Examiner—John M. Ford
Assistant Examiner—Robert C. Whittenbaugh
Attorney, Agent, or Firm—Abelman Frayne Rezac & Schwab

[57] ABSTRACT

4-Thioquinazoline derivatives of formula (I) are provided.

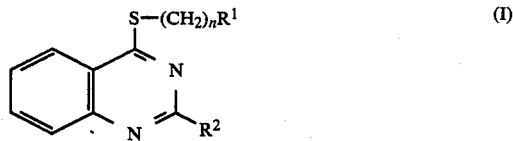

wherein $R^1$ is a $C_1$–$C_6$ alkylamino group, a phenyl group, a substituted phenyl group or a 5- or 6-membered heterocyclic group containing one or two N, O or S as a hetero atom or atoms, said heterocyclic group optionally being substituted or fused with a benzene ring; n is 1 or 2; or $R^2$ is a hydrogen atom or a $C_1$–$C_6$ alkyl group, and pharmaceutically acceptable acid addition salts thereof. They are useful as antiulcer agents.

6 Claims, No Drawings

4-THIOQUINAZOLINE DERIVATIVES AS ANTIULCER AGENTS

FIELD OF THE INVENTION

The present invention relates to new 4-thioquinazoline derivatives, processes for their preparation and their use as antiulcer agents.

BACKGROUND OF THE INVENTION

The agents used as the antiulcer drugs include $H_2$-receptor antagonists, anticholinergic agents, gastric mucosal protective agents and antacids, which are used depending upon the symptom of patients. These known agents, however, are of such drawbacks as generally weak activity and frequent occurrence of side effects.

For example, cimetidine, which is a $H_2$-receptor antagonist widely employed, is known to have side effects such as gynecomatism. Moreover, numbers of cases are reported about recurrence of ulcer after suspension of administration with cimetidine. Anticholinergic agents are known to have such side effects as suppression of gastric motility, corediastasis and thirst. Furthermore, they exhibit activity only for a limited period of time. Antacids are known to have frequent occurrence of such side effects as constipation.

As described above, known antiulcer agents were limitedly used in terms of manner of administration due to their side effects, and they have common drawback of exhibiting somewhat weak activity.

Quinoxalinyl esters of carbamimidothioic acids are disclosed in Chem. Abstr. vol. 97, 216239k (1982), which are prepared by reacting 2-chloroquinoxalines with thioureas and useful as gastric secretion inhibitors and antihypertensives (no data).

The present invention results from efforts to develop new 4-thioquinazoline derivatives with more improved antiulcer effect.

DISCLOSURE OF THE INVENTION

According to the invention, there are provided 4-thioquinazoline derivatives of formula (I)

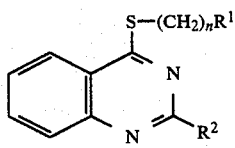
(I)

wherein $R^1$ is a $C_1$–$C_6$ alkylamino group, a phenyl group, a substituted phenyl group or a 5- or 6-membered heterocyclic group containing one or two N, O or S as a hetero atom or atoms, said heterocyclic group optionally being substituted or fused with a benzene ring; n is 1 or 2; or $R^2$ is a hydrogen atom or a $C_1$–$C_6$ alkyl group, and pharmaceutically acceptable acid addition salts thereof.

In the above formula (I), where $R^1$ is a $C_1$–$C_6$ alkylamino group, it includes e.g., a di-$C_1$–$C_6$ alkylamino group such as dimethylamino, diethylamino, etc. Where $R^1$ is a substituted phenyl group, the substituent or substituents include e.g., a $C_1$–$C_6$ alkylamino group such as di-$C_1$–$C_6$ alkylamino group (e.g., dimethylamino) and a $C_1$–$C_6$ alkoxy group (e.g., trimethoxy). Thus, the substituted phenyl group includes e.g., dimethylaminophenyl and trimethoxyphenyl.

Where $R^1$ is a 5- or 6-membered heterocyclic group, it includes e.g., furyl, thienyl, benzimidazolyl, pyridyl (e.g., 2-, 3- or 4-pyridyl) and quinolyl. The 5- or 6-membered heterocyclic group may be substituted with at least one $C_1$–$C_6$ alkyl and/or $C_1$–$C_6$ alkoxy group. The $C_1$–$C_6$ alkyl group includes e.g., methyl, ethyl, propyl, isopropyl, butyl, isobutyl, pentyl and hexyl. The $C_1$–$C_6$ alkoxy group includes e.g., methoxy, ethoxy, propoxy, isopropoxy, butoxy, isobutoxy, pentyloxy and hexyloxy.

Where $R^2$ is a $C_1$–$C_6$ alkyl group, it includes the same groups as recited above.

Representative examples of the compounds represented by formula (I) are given hereinbelow.

4-(2-Pyridylmethylthio)-quinazoline,
4-(2-(Diethylamino)ethylthio)-quinazoline,
4-(2-Benzimidazolylmethylthio)-quinazoline,
4-Benzylthio-quinazoline,
4-(2-Furylmethylthio)-quinazoline,
4-(2-Thienylmethylthio)-quinazoline,
4-(3,4,5-Trimethoxybenzylthio)-quinazoline,
4-(2-Dimethylaminobenzylthio)-quinazoline,
4-(4-Pyridylmethylthio)-quinazoline,
4-(2-Quinolylmethylthio)-quinazoline,
4-[(4-Methylpyridin-2-yl)methylthio]-quinazoline,
4-[(4-Methoxy-5-methylpyridin-2-yl)methylthio]-quinazoline,
4-[(4-Methoxy-5-methylpyridin-2-yl)methylthio]-2-methylquinazoline, and
4-(3-Pyridylmethylthio)-quinazoline.

The compounds of formula (I) according to the invention can be prepared by reacting a compound of formula (II)

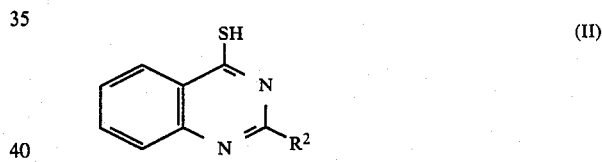
(II)

wherein $R^2$ has the same meaning as defined above, with a compound of formula (III)

$$X-(CH_2)_nR^1 \qquad (III)$$

wherein $R^1$ and n have the same meanings as defined above and X is a halogen atom in the presence of a base. The halogen atom includes chlorine, bromine and iodine.

The bases used in the reaction of the compounds (II) and (III) include e.g., inorganic bases such as sodium hydroxide, potassium hydroxide or sodium carbonate, organic bases such as diethylamine, triethylamine or pyridine, and alkali metal alkoxides such as sodium methoxide, potassium methoxide, sodium ethoxide or potassium t-butoxide.

In performing the reaction, the compound (III) may be used in the proportion of from 0.5 to 5 moles per mole of the compound (II). Generally, however, it is preferable that the compound (III) is used in equal or excess amount to the compound (II). For example, the compound (III) is preferably used in the proportion of from 1 to 3 moles per mole of the compound (II).

The reaction can be carried out in water or various organic solvents. The organic solvents include for example lower alcohols such as methanol, ethanol or butanol; polar solvents such as dimethyl sulfoxide or dimethylformamide; ethers such as ether, tetrahydrofuran or dioxane; esters such as ethyl acetate or butyl acetate; ketones such as acetone or ethyl methyl ketone; or mixtures thereof. Preferably, the above reaction is carried out in a mixed solvent of water with any one of the solvents described above.

Normally, the reaction is performed at temperatures between room temperature and 150° C., preferably between room temperature and the reflux temperature of the reaction mixture.

The compounds of formula (I) may be converted, if desired, to pharmaceutically acceptable acid addition salts thereof, and these salts are embraced within the scope of this invention.

Concrete examples of addition salts include the salts of the compounds with inorganic acids such as hydrochloric acid, hydrobromic acid, hydroiodic acid, nitric acid, sulfuric acid or phosphoric acid, and organic acids such as formic acid, acetic acid, propionic acid, butyric acid, maleic acid, fumaric acid, malonic acid, malic acid, citric acid, tartaric acid or oxalic acid.

The compounds of formula (I) and pharmaceutically acceptable acid addition salts thereof are of prominent antiulcer activity.

Thus, the present invention also relates to pharmaceutical compositions which comprise as an active ingredient the compounds of formula (I) or pharmaceutically acceptable acid addition salts thereof.

The pharmaceutical compositions of the invention may by formulated into various forms which are commonly used in the art and which are administered orally or parenterally. For example, they may be formulated into tablets, capsules, suppositories, troches, syrups, creams, ointments, granules, powders, injectable solutions or suspensions. Alternatively, they may be formulated into double or multiple layer tablets, together with other active principles. Furthermore, they may be formulated into coated tablets such as sugar-coated tablets, enteric-coated tablets and film-coated tablets.

In order to obtain solid preparations, the compounds of this invention are mixed with such conventional diluents or fillers as lactose, refined sugar, crystalline cellulose, corn starch, calcium phosphate, sorbitol, glycine, carboxymethylcellulose, gum arabic, polyvinylpyrrolidone, hydroxypropylcellulose, glycerol, polyethylene glycol, stearic acid, magnesium stearate or talc.

In order to obtain semi-solid preparations, the compounds of this invention are mixed with such additives as plant wax, synthetic wax or fats.

In order to obtain liquid preparations, the compounds of this invention are mixed with such diluents or additives as sodium chloride, sorbitol, glycerol, olive oil, almond oil, propylene glycol or ethanol.

The compounds of the invention may normally be contained in a preparation in an amount of from 0.1 to 100% by weight, more suitably in an amount of from 1 to 50% by weight in the case of preparations for oral administration and from 0.2 to 20% by weight in the case of injectable preparations.

There is no particular limitation as to the method of administration and the dosage of the antiulcer agents according to the invention. They are chosen, depending on the form of preparation, age of patients, sex, degree of symptom, etc. Normally, however, the dosage will be in the range of from 10 to 1,000 mg per day.

The pharmaceutical composition of the invention may be administered in conjunction with one or more other active principles such as antacids, non-steroid anti-inflammatory agents or other types of antiulcer agents.

The invention will be explained in more detail by the following Examples, which are to be understood not to limit the scope of this invention.

EXAMPLE 1

4-(2-Pyridylmethylthio)-quinazoline 8.4 ml of 28% methanolic solution of sodium methoxide were added to a solution of 3.52 g of 4-mercaptoquinazoline and 3.54 g of 2-chloromethylpyridine hydrochloride in 50 ml of methanol and stirred at room temperature for 3 days.

To a reaction solution was added water and the solution was extracted with chloroform. The chloroform layer was washed with an aqueous sodium carbonate solution, dehydrated with sodium sulfate and distilled off under reduced pressure. The residue was purified by silica gel column chromatography with a 2:3 mixed solution of ethyl acetate and chloroform as an eluent and the eluate was crystallized from isopropyl ether to give 2.76 g of the title compound.

Pale yellow crystals
M.P. 64.9°–66.2° C.
NMR(CDCl$_3$,δ): 4.80(2H,s), 7.13–7.23(1H,m), 7.50–7.70(3H,m), 7.85(1H,t), 7.95(1H,d), 8.12(1H,d), 8.60(1H,d), 9.01(1H,s)
IR(Nujol,cm$^{-1}$): 1610, 1590

EXAMPLE 2

The following compounds (a) to (i) were prepared in an analogous manner to that of Example 1.

(a) 4-(2-Benzimidazolylmethylthio)-quinazoline

The title compound(2.5 g) was prepared from 4-mercaptoquinazoline(6.0 g) and 2-chloromethylbenzimidazole (2.52 g).

Pale yellow crystals (from benzene)
M.P. 113.0°–117.0° C.
NMR(CDCl$_3$,δ): 4.82(2H,s), 7.18–7.29(3H,m), 7.51–7.66(3H,m), 7.83–8.06(3H,m), 9.14(1H,s)
IR(Nujol,cm$^{-1}$): 1620, 1600

(b) 4-[2-(Diethylamino)ethylthio]-quinazoline

The title compound(4.82 g) was prepared from 4-mercaptoquinazoline(5.0 g) and N,N-diethylaminoethylchloride hydrochloride(5.3 g).

Yellow oily product
NMR(CDCl$_3$,δ): 1.10(6H,t,J=7 Hz), 2.66(4H,q,J=7 Hz), 2.80–2.90(2H,m), 3.41–3.53(2H,m), 7.55(1H,t), 7.83(1H,t), 7.94(1H,d), 8.09(1H,d), 8.98(1H,s)
IR(neat,cm$^{-1}$): 1620, 1600

(c) 4-Benzylthio-quinazoline

The title compound(5.2 g) was prepared from 4-mercaptoquinazoline(7.0 g) and benzyl chloride(5.5 g).

Pale yellow needles (from isopropyl ether)
M.P. 103.0°–105.1° C.
NMR(CDCl$_3$,δ): 4.65(2H,s), 7.21–7.61(6H,m), 7.78–8.08(3H,m), 9.02(1H,s)
IR(Nujol,cm$^{-1}$): 1615, 1570

(d) 4-(2-Furylmethylthio)-quinazoline

The title compound(3.69 g) was prepared from 4-mercaptoquinazoline(5.0 g) and 2-chloromethylfuran(5.4 g).

Orange yellow crystals (from isopropyl ether)
M.P. 86.2°–87.6° C.

NMR(CDCl$_3$,δ): 4.71(2H,s), 6.28–6.40(2H,m), 7.33–7.39(1H,m), 7.50–7.61(1H,m), 7.78–8.08(3H,m), 9.02(1H,s)

IR(Nujol,cm$^{-1}$): 1610, 1570

(e) 4-(2-Thienylmethylthio)-quinazoline

The title compound(1.82 g) was prepared from 4-mercaptoquinazoline(5.0 g) and 2-bromomethylthiophene(8.15 g).

Pale yellow crystals (from isopropyl ether)
M.P. 52.4°–59.7° C.

NMR(CDCl$_3$,δ): 4.88(2H,s), 6.90–6.97(1H,m), 7.09–7.23(2H,m), 7.57(1H,t), 7.84(1H,t), 7.93–8.08(2H,m), 9.05(1H,s)

IR(Nujol,cm$^{-1}$): 1620, 1565

(f) 4-(3,4,5-Trimethoxybenzylthio)-quinazoline

The title compound(3.56 g) was prepared from 4-mercaptoquinazoline(4.0 g) and 3,4,5-trimethoxybenzyl chloride(7.3 g).

Pale yellow crystals (from benzene/isopropyl ether)
M.P. 134.4°–137.0° C.

NMR(CDCl$_3$,δ): 3.82(3H,s), 3.86(6H,s), 4.60(2H,s), 6.71(2H,s), 7.58(1H,t), 7.86(1H,t), 7.98(1H,d), 8.07(1H,d), 9.03(1H,s)

IR(Nujol, cm$^{-1}$): 1600, 1570

(g) 4-(2-Dimethylaminobenzylthio)-quinazoline

The title compound(1.31 g) was prepared from 4-mercaptoquinazoline(3.0 g) and 2-dimethylamino benzyl chloride(6.1 g).

Pale yellow crystals (from isopropyl ether)
M.P. 79.0°–81.9° C.

NMR(CDCl$_3$,δ): 2.76(6H,s), 4.80(2H,s), 6.99–7.32(3H,m), 7.47–7.60(2H,m), 7.82(1H,t), 7.96(1H,d), 8.08(1H,d), 9.03(1H,s)

IR(Nujol,cm$^{-1}$): 1610, 1600

EXAMPLE 3

4-(4-Pyridylmethylthio)-quinazoline 13.1 ml of 28% methanolic solution of sodium methoxide were added to a solution of 5.25 g of 4-mercaptoquinazoline and 5.28 g of 4-chloromethylpyridine hydrochloride in 50 ml of methanol and stirred at room temperature for 8 hours.

To a reaction solution was added water and the solution was extracted with chloroform. The chloroform layer was washed with an aqueous sodium carbonate solution, dehydrated with sodium sulfate and evaporated off. The residue was dissolved in chloroform, about 0.5 g of activated charcoal was added to a solution and a mixture was heated at 50° C. for 30 minutes. After allowing to cool, activated charcoal was filtered off and then chloroform was distilled off. Crystallization of the residue from ethyl acetate gave 3.40 g of the title compound.

Yellow crystals
M.P. 116.9°–118.1° C.

NMR(CDCl$_3$,δ): 4.61(2H,s), 7.37–7.43(2H,m), 7.55–7.63(1H,m), 7.81–8.08(3H,m), 8.00–8.08(2H,m), 9.02(1H,s),

IR(Nujol,cm$^{-1}$): 1620, 1605

EXAMPLE 4

4-(2-Quinolylmethylthio)-quinazoline

The title compound(1.26 g) was prepared from 4-mercaptoquinazline(1.82 g) and 2-chloromethylquinoline hydrochloride(2.0 g) in an analogous manner to that of Example 3.

Orange yellow crystals (from isopropyl ether)
M.P. 119.1°–120.7° C.

NMR(CDCl$_3$,δ): 5.00(2H,s), 7.46–8.16(10H,m), 9.03(1H,s)

IR(Nujol,cm$^{-1}$): 1620, 1600

EXAMPLE 5

4-[(4-Methylpyridin-2-yl)methylthio]-quinazoline 13 ml of 28% methanolic solution of sodium methoxide were added to a solution of 5.0 g of 4-mercaptoquinazoline and 5.5 g of 2-chloromethyl-4-methylpyridine hydrochloride in 50 ml of methanol and stirred at room temperature for 5 hours. A reaction solution was poured into water and extracted with chloroform. The chloroform layer was washed with an aqueous sodium carbonate solution, dried over sodium sulfate and distilled off under reduced pressure. The residue was purified by silica gel column chromatography. The fraction eluted with 10% ethyl acetate/chloroform was crystallized from isopropyl ether to obtain 1.84 g (22.3%) of the title compound.

White crystals
M.P.(dec) 77.5°–79.4° C.

NMR(CDCl$_3$,δ): 2.33(3H,s), 4.78(2H,s), 7.01(1H,d), 7.34(1H,s), 7.58(1H,t), 7.85(1H,t), 7.96(1H,d), 8.12(1H,d), 8.45(1H,d), 9.01(1H,s)

IR(Nujol,cm$^{-1}$): 1610

EXAMPLE 6

The following compounds (a) to (c) were prepared in an analogous manner to that of Example 5.

(a)

4-[(4-Methoxy-5-methylpyridin-2-yl)methylthio]-quinazoline

The title compound(0.24 g) was prepared from 4-mercaptoquinazoline(3.5 g) and 2-chloromethyl-4-methoxy-5-methylpyridine(4.1 g).

Yellow crystals (from isopropyl ether)
M.P. 140.7°–142.6° C.

NMR(CDCl$_3$,δ): 2.14(3H,s), 3.85(3H,s), 4.74(2H,s), 7.03(1H,s), 7.58(1H,t), 7.85(1H,t), 7.96(1H,d), 8.11(1H,d), 8.21(1H,s), 9.01(1H,s)

IR(Nujol,cm$^{-1}$): 1600

(b)

4-[(4-Methoxy-5-methylpyridin-2-yl)methylthio]-2-methylquinazoline

The title compound(0.12 g) was prepared from 4-mercapto-2-methylquinazoline(4.48 g) and 2-chloromethyl-4-methoxy-5-methylpyridine(6.3 g).

Yellow crystals (from isopropyl ether)
M.P. 131.9°–133.7° C.

NMR(CDCl$_3$,δ): 2.33(3H,s), 2.81(3H,s), 3.89(3H,s), 4.85(2H,s), 6.74(1H,d), 7.48(1H,t), 7.71–7.91(2H,m), 8.06(1H,d), 8.36(1H,d)

IR(Nujol,cm$^{-1}$): 1615

(c) 4-(3-Pyridylmethylthio)-quinazoline

The title compound(3.34 g) was prepared from 4-mercaptoquinazoline(6.0 g) and 3-chloromethylpyridine(5.2 g).

Yellow crystals (from isopropyl ether)
M.P. 93.7°-97.0° C.
NMR(CDCl$_3$,δ): 4.64(2H,s), 7.21-7.31(1H,m), 7.59(1H,t), 7.78-8.10(4H,m), 8.51(1H,d), 8.76(1H,s), 9.02(1H,s)
IR(Nujol,cm$^{-1}$): 1610

EXAMPLE 7

The antiulcer activity of the compounds of this invention was determined by the following method.

Four-week-old ddy series male mice were used as the test animals after they were fasted for 24 hours. Each test compound suspended in a 1% gum arabic solution was administered to the stomach of each mouse at a dose of 100 mg/kg, and then, after 30 minutes, 20 mg/kg of indomethacin was administered orally. Four hours after the administration of indomethacin, the stomach of mouse was extirpated and the length of ulcers was measured. Then, the ulcer index was determined by the total sum of the scores as calculated in Table 1.

TABLE 1

| Length of ulcer | 0.5mm < | 1mm < | 21mm < | 3mm < |
| --- | --- | --- | --- | --- |
| Score | 0.5 | 1 | 2 | 3 |

The mean ulcer index of each group was calculated and the suppression rate against the control group in terms of difference in the mean ulcer index was determined. The results are shown in Table 2.

TABLE 2

| Compound tested | Suppression rate of indomethacin induced ulcer, 100 mg/kg, p.o. |
| --- | --- |
| 4-(2-Pyridylmethylthio)-quinazoline | 94 |
| 4-[2-(Diethylamino)ethylthio]-quinazoline | 49 |
| 4-(4-Pyridylmethylthio)-quinazoline | 92 |
| 4-(2-Quinolylmethylthio)-quinazoline | 70 |
| 4-[(4-Methylpyridin-2-yl)methylthio]-quinazoline | 70 |
| 4-[(4-Methoxy-5-methylpyridin-2-yl)-methylthio]-quinazoline | 81 |
| Cimetidine (control) | 40 |

As shown in Table 2, it is evident that the compounds of the invention possess prominent antiulcer activity in comparison with cimetidine.

The compounds of this invention have generally low toxicity. For example, LD$_{50}$ value(P.O.) of 4-(2-pyridylmethylthio)-quinazoline is higher than 1 g/kg. The reversion test on the compound reveals the negative result.

Furthermore, similar test was carried out with respect to other compounds of the present invention than those shown in Table 2. As a result, other compounds were found to possess the antiulcer activity.

Examples in which the compounds of the present invention are formulated into various preparations are illustrated below.

Preparation 1. Tablet 50 mg of 4-(2-pyridylmethylthio)-quinazoline, 77 mg of lactose, 15 mg of crystalline cellulose, 7 mg of corn starch and 1 mg of magnesium stearate (each per tablet) were thoroughly mixed, and then the mixture was tableted with a rotary tableting machine into a tablet of 7mm diameter, weight 150 mg.

Preparation 2. Granule 50 mg of 4-(2-pyridylmethylthio)-quinazoline, 230 mg of lactose, 110 mg of corn starch and 100 mg of crystalline cellulose were thoroughly mixed. Meanwhile, 10 mg of hydroxypropylcellulose were dissolved in 90 mg of ethanol and the solution was added to the previously prepared mixture. The whole mixture was kneaded and granulated. The granules were air-dried at 50° C. and then sieved into the grain size of from 297 μm to 1460 μm. 500 mg of the granules were packed into a unit dosage form.

Preparation 3. Syrup 5 g of 4-(2-pyridylmethylthio)-quinazoline, 30 g of refined sugar, 25 g of 70 w/v % D-sorbitol, 0.03 g of ethyl p-hydroxybenzoate and 0.015 g of propyl p-hydroxybenzoate were dissolved in 60 ml of warmed water. After the solution was cooled, a solution of 0.2 g of a flavor in 0.15 g of glycerol and 0.5 g of 96% ethanol was added. The whole mixture was diluted with water to balance 100 ml.

Preparation 4. Injectable solution 5 mg of 4-(2-pyridylmethylthio)-quinazoline and 10 mg of sodium chloride were dissolved in sterilized distilled water to balance 1 ml.

Preparation 5. Suppository 20 g of polyethylene glycol 4000 were added to a solution of 10 g of 4-(2-pyridylmethylthio)-quinazoline in 70 g of glycerol. The mixture was warmed and poured into a suppository mold and then cooled to give suppositories, each weighing 1.5 g.

What is claimed is:

1. A compound of the Formula (I)

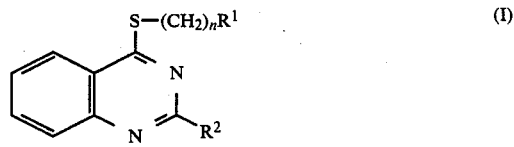

wherein R$^1$ is a C$_1$-C$_6$ alkylamino group; a phenyl group optionally substituted by a C$_1$-C$_6$ alkylamino or a C$_1$-C$_6$ alkoxy group; furyl; thienyl; benzimidazolyl; quinolyl; or pyridyl optionally substituted at a carbon atom by at least one of C$_1$-C$_6$ alkyl and C$_1$-C$_6$ alkoxy groups; n is 1 or 2; and R$^2$ is a hydrogen atom or a C$_1$-C$_6$ alkyl group, or a pharmaceutically acceptable acid addition salt thereof.

2. A compound of claim 1 wherein R$^1$ is di-C$_1$-C$_4$ alkylamino, phenyl, C$_1$-C$_4$ alkoxy-substituted phenyl or C$_1$-C$_4$ alkylamino-substituted phenyl.

3. A pharmaceutial composition useful as an antiulcer agent which comprises a therapeutically effective amount of a coumpound of claim 1 or a pharmaceutically acceptable acid addition salt therof, optionally in admixture with additives for pharmaceutical preparation.

4. A pharmaceutical composition useful as an anti-ulcer agent which comprises a therapeutically effective amount of a compound of claim 1 wherein $R^1$ is di-$C_1$-$C_4$ alkylamino, phenyl, $C_1$-$C_4$ alkoxy-substituted phenyl, $C_1$-$C_4$ alkylamino-substituted phenyl, furyl, thienyl, benzimidazolyl, pyridyl, $C_1$-$C_4$ alkyl-substituted pyridyl, $C_1$-$C_4$ alkyl and $C_1$-$C_4$ alkoxy-substituted pyridyl or quinolyl and $R^2$ is hydrogen or $C_1$-$C_4$ alkyl, or a pharmaceutically acceptable acid addition salt thereof, optionally in admixture with additives for pharmaceutical preparation.

5. A compound of claim 1 wherein $R^1$ is furyl, thienyl, benzimidazolyl, pyridyl, $C_1$-$C_4$ alkyl substituted pyridyl, $C_1$-$C_4$ alkyl and $C_1$-$C_4$ alkoxy-substituted pyridyl or quinolyl.

6. A compound of claim 1 wherein $R^2$ is hydrogen or $C_1$-$C_4$ alkyl.

* * * * *